United States Patent

Garito et al.

Patent Number: 5,954,686
Date of Patent: Sep. 21, 1999

[54] DUAL-FREQUENCY ELECTROSURGICAL INSTRUMENT

[76] Inventors: Jon C Garito; Alan G. Ellman, both of 1135 Railroad Ave., Hewlett, N.Y. 11557

[21] Appl. No.: 09/017,235

[22] Filed: Feb. 2, 1998

[51] Int. Cl.⁶ .................................................. A61B 17/39
[52] U.S. Cl. ................................. 604/37; 606/39; 606/40
[58] Field of Search .................................. 606/34, 37–40

[56] References Cited

U.S. PATENT DOCUMENTS

| | | | |
|---|---|---|---|
| 4,051,855 | 10/1977 | Schneiderman | 606/37 |
| 4,148,321 | 4/1979 | Wyss et al. . | |
| 4,171,700 | 10/1979 | Farin | 606/35 |
| 4,312,364 | 1/1982 | Convert et al. . | |
| 4,346,716 | 8/1982 | Carr . | |
| 4,438,766 | 3/1984 | Bowers | 606/37 |
| 4,463,759 | 8/1984 | Garito et al. . | |
| 4,557,272 | 12/1985 | Carr . | |
| 4,658,820 | 4/1987 | Klicek . | |
| 4,936,281 | 6/1990 | Stasz . | |
| 5,396,893 | 3/1995 | Oberg et al. . | |
| 5,413,574 | 5/1995 | Fugo . | |
| 5,478,303 | 12/1995 | Foley-Nolan et al. . | |
| 5,562,503 | 10/1996 | Ellman et al. . | |

FOREIGN PATENT DOCUMENTS

| | | | |
|---|---|---|---|
| 2154881 | 9/1985 | United Kingdom | 606/37 |

*Primary Examiner*—Lee Cohen

[57] ABSTRACT

An electrosurgical instrument that is capable of generating high-quality RF energy at a first frequency best suited for delicate, precise. and quick-healing cutting procedures with low leakage currents using a unipolar handpiece, and also provides high-quality RF energy at a second frequency best suited for coagulation for use with a bipolar handpiece. In a preferred embodiment, the first frequency is in the range of about 3.8–4.0 Mhz, and the second frequency is in the range of about 1.7–2.0 Mhz. The instrument is preferably configured so that both a unipolar handpiece and a bipolar handpiece can be used during a surgical procedure, though not at the same time, without having to activate any switches on the instrument. This has the advantage of providing the surgeon all the benefits of both electrosurgical modes while not jeopardizing the crucial sterile field.

12 Claims, 3 Drawing Sheets

DUAL-FREQUENCY ELECTROSURGICAL INSTRUMENT

The invention is directed to an electrosurgical instrument or apparatus, and in particular to an electrosurgical instrument that operates with two different frequencies.

BACKGROUND OF INVENTION

Electrosurgical instruments are well known and widely used in the medical, dental, and veterinarian fields. They offer the capability of precision cutting with electrosurgical currents in the megacycle range using a handpiece with needle, ball, or loop electrodes in a unipolar operating mode, or convenient coagulation using a forceps in a bipolar operating mode. Ellman International, Inc. makes available an electrosurgical instrument which provides on its front panel connectors for receiving the plug of a unipolar handpiece and a ground or indifferent plate, as well as connectors for receiving the plugs of a bipolar forceps.

In a typical surgical setting, a surgeon may first use the unipolar handpiece to perform a desired cutting procedure and then desire to use the bipolar forceps for coagulation of blood vessels because of its unique ability to coagulate in a fluid field. This creates problems in maintaining the requisite sterile field while still allowing the surgeon to unplug and plug in different devices from or to the instrument. One possible solution is described in U.S. Pat. No. 5,562,503, whose contents are herein incorporated by reference. In the solution proposed in this patent, an adaptor apparatus is provided and configured to plug directly into the connectors on the electrosurgical instrument, and provided with connector means for receiving mating connectors of both the unipolar handpiece and the bipolar forceps. Switch means are provided on the adaptor apparatus for allowing the surgeon to easily switch over from the unipolar to the bipolar mode by simply throwing the switch. Since the adaptor can be attached to the electrosurgical instrument and the unipolar handpiece and bipolar forceps both attached to the adaptor before the sterile field is created, only the switch handle need be touched to switch between the two modes, and the switch handle can easily be sterilized. Alternatively, the surgeon can use an elbow to throw the switch without spoiling the sterile field.

However, the instrument described in this patent uses a single frequency for the operating modes when using either a unipolar handpiece or a bipolar handpiece. This is not always optimum for both cutting and coagulation. Moreover, certain applications require an instrument which provides high output radio-frequency (RF) energy for delicate, precise, and quick-healing cutting procedures, but with low leakage currents. To the best of our knowledge, there is no commercially-available instrument that provides high output radio-frequency (RF) energy for delicate, precise, and quick-healing cutting procedures with low leakage currents using a unipolar handpiece, and also provides high-quality RF energy best suited for coagulation for use with a bipolar handpiece.

SUMMARY OF INVENTION

The principal object of the invention is an electrosurgical instrument capable of providing optimal RF energy for both cutting and coagulation using either the unipolar or bipolar mode of the instrument.

These objects are achieved in accordance with one aspect of the invention by an electrosurgical instrument that is capable of generating high-quality RF energy at a first frequency best suited for delicate, precise, and quick-healing cutting procedures with low leakage currents using a unipolar handpiece, and also provides high-quality RF energy at a second frequency best suited for coagulation for use with a bipolar handpiece.

In a preferred embodiment, the first frequency is in the range of about 3.8–4.0 Mhz, and the second frequency is in the range of about 1.7–2.0 Mhz.

In another preferred embodiment, the first and second frequencies are derived by division upon selection from RF generators at higher third and fourth frequencies, respectively, which simplifies the RF generator selection circuitry.

In accordance with a further aspect of the invention, the instrument is configured so that both a unipolar handpiece and a bipolar handpiece can be used during a surgical procedure, though not at the same time, without having to activate any switches on the instrument. This has the advantage of providing the surgeon all the benefits of both electrosurgical modes while not jeopardizing the crucial sterile field.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention, like reference numerals or letters signifying the same or similar components.

DETAILED DESCRIPTION OF PREFERRED EMBODIMENTS

Figure 1:
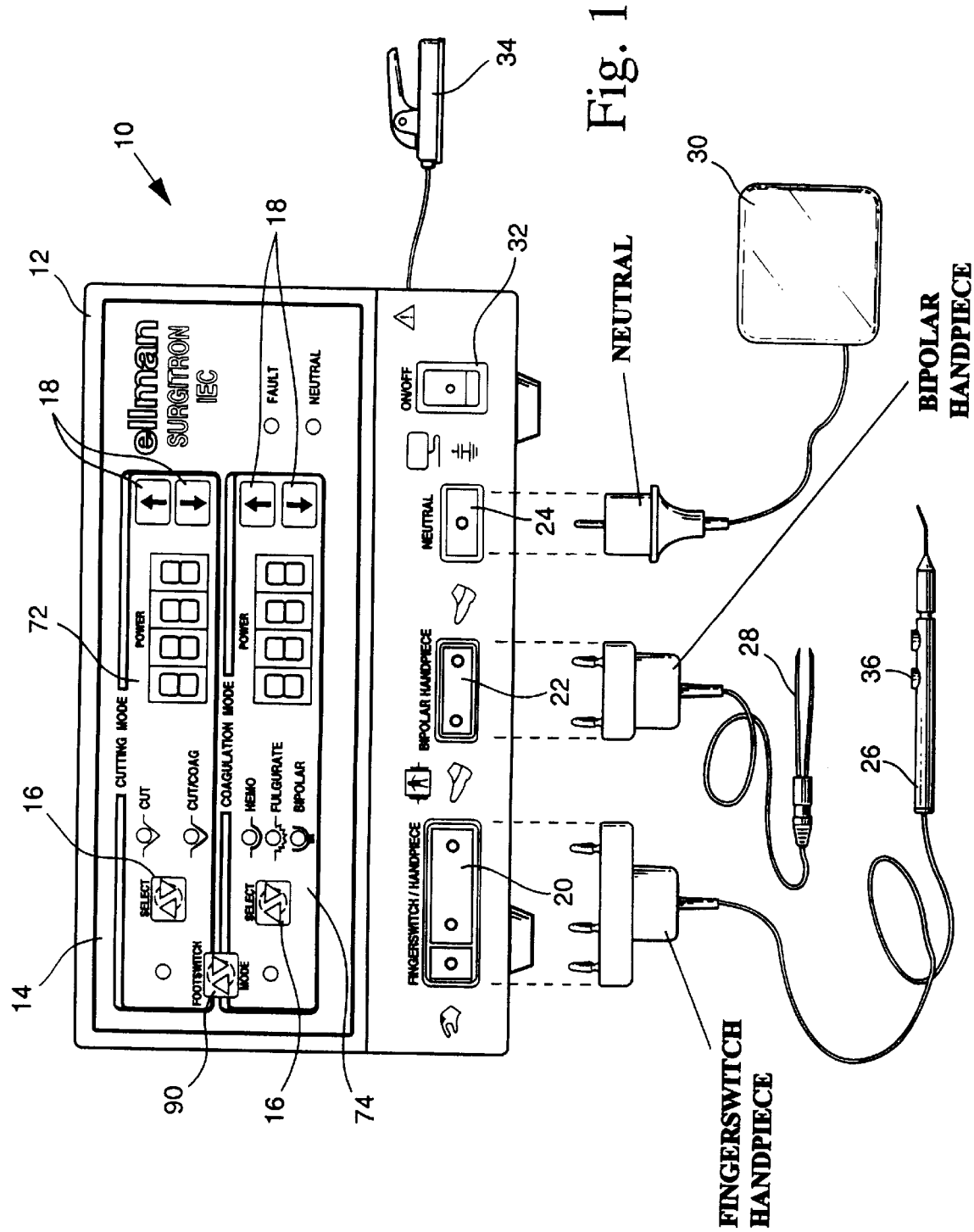
FIG. 1 is a schematic view of one form of electrosurgical instrument in accordance with the invention.

One form of the electrosurgical instrument 10 according to the invention is illustrated in FIG. 1. It comprises a console unit 12 having a box-like housing comprising at the front a control panel 14 for the instrument. The control panel includes touch switches 90 for selecting cutting or coagulation modes and touch switches 18 for controlling the power output, indicated by upper and lower digital displays showing all 8's. At the bottom are output female connectors 20, 22, 24 for plugging in, respectively, at the left, a fingerswitch-controlled unipolar handpiece 26; at the center, a bipolar handpiece or forceps 28; and at the right a single or split neutral plate 30. An on-off power switch 32 is at the far right. The circuitry used to provide a fingerswitch-controlled unipolar handpiece may be of the type described in connection with the control unit 50 of U.S. Pat. No. 4,463,759, whose contents are herein incorporated by reference, which circuitry is in this case incorporated in the console unit 12. A connector (not shown) is provided at the side for receiving a conventional footswitch 34. A feature of the invention is that both the unipolar and bipolar handpieces can be simultaneously connected to the console unit 12 and operated in any order without touching the console unit or the control panel when the control panel has been preset or activated at the desired powers for each of the handpieces. For example, if the surgeon determines that s/he is going to perform a cutting procedure with a particular electrode, then s/he can preset the cutting mode power on the upper digital display to, say, 80 watts by the up/down buttons 18. (Typically, these units are designed to supply up to 100 watts of RF power to either handpiece.) For coagulation with the bipolar handpiece, s/he may desire to use, say, 50 watts, which can also be preset on the lower digital display by the up/down buttons 18. The internal circuitry is controlled so that, when the fingerswitch unipolar handpiece is used, then RF power can be supplied to the electrode in the unipolar handpiece when a fingerswitch 36 on the handpiece 26 is depressed. However, when it is desired to use the bipolar handpiece 28, then the footswitch 34 is depressed, which then supplies RF power to the forceps of the bipolar handpiece. This unusual result is a consequence of software control such that, while the machine mode is selected such that the fingerswitches on the unipolar handpiece can be used to apply power to the electrode (footswitch mode non-selected), only the footswitch can be used to apply power to the bipolar handpiece. This prevents power selected for the unipolar handpiece to be applied to the bipolar handpiece, and vice-versa. On the other hand, when it is not intended to use the bipolar handpiece and the footswitch mode is selected, then the footswitch can be used to operate the unipolar handpiece.

Figure 2:
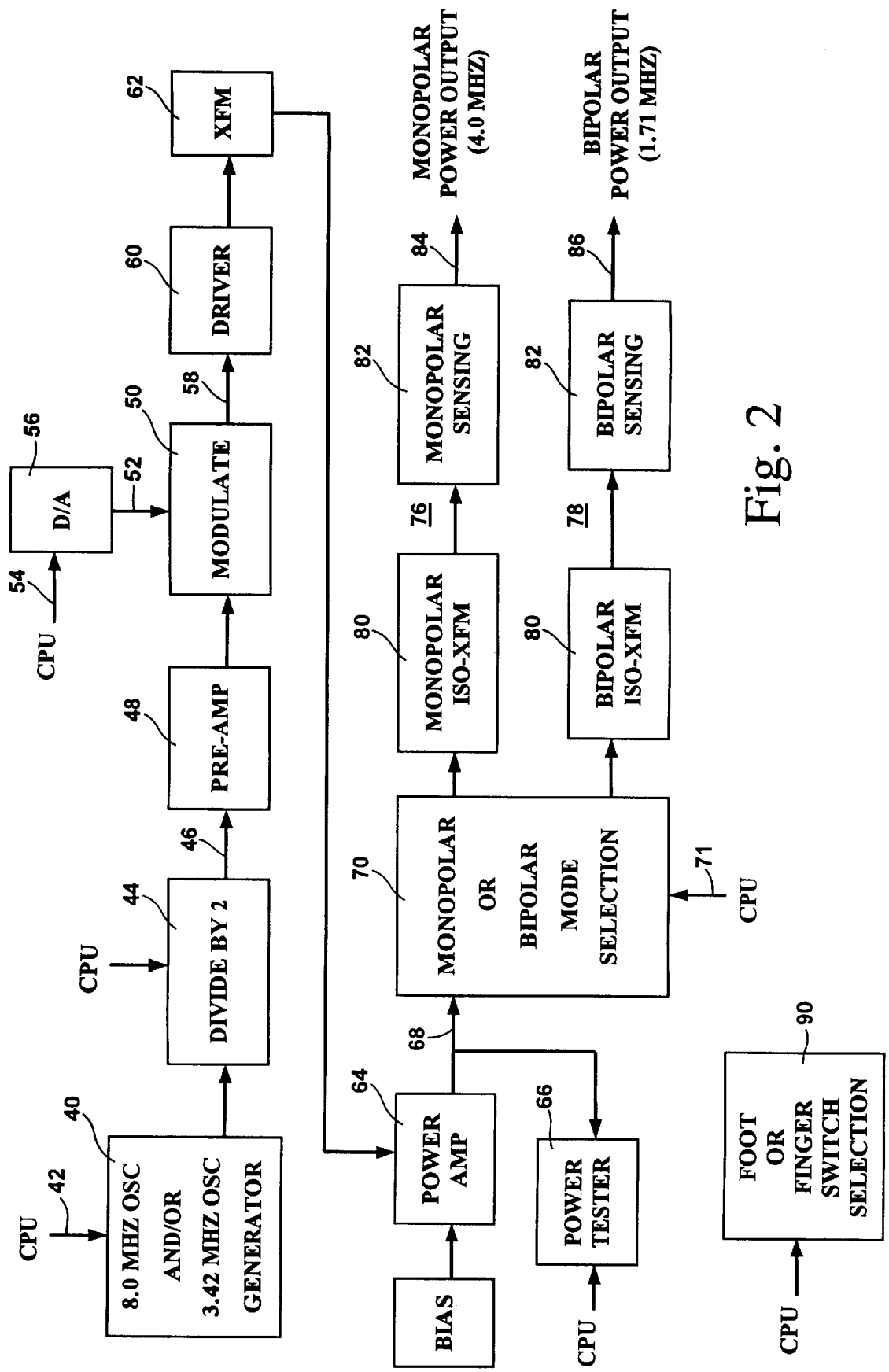
FIG. 2 is a circuit block diagram of one form of system circuitry for the electrosurgical instrument of FIG. 1.

One form of the RF circuitry to achieve the foregoing operation is illustrated in the block diagram of FIG. 2. The block 40 in the upper left contains two independent conventional RF oscillators generating, preferably, RF oscillations at 8.0 and 3.42 Mhz respectively, previously referred to as the third and fourth frequencies. As will be explained in greater detail below, the double arrows 42 labelled CPU represents a selection signal generated by a conventional microcontroller under software control and inputted into the block 40 to select for operation either the 8.0 MHz oscillator or the 3.42 MHz oscillator. Both oscillators are constantly on when the power switch is activated, and the CPU selection 42 determines which of the third or fourth frequencies are outputted to the divide-by-2 block 44, resulting in an RF carrier 46 at either the first (4.0) or the second (1.71) frequency. That carrier is then pre-amplified in block 48 and inputted to a conventional modulator stage 50. Also input to the modulator stage is a modulating signal 52 derived from a CPU selection signal 54 and a D/A converter 56. The modulations referred to are the different output waveforms used for the known CUT, CUT/COAG, HEMO, and FULGURATE modes. These typically are: CUT-CW (full-wave rectified and filtered) output with maximum average power; CUT/COAG -full-wave rectified but unfiltered, deeply modulated, at 37.5 or 75 Hz rate, envelope with approximately 70% average to peak power ratio; HEMO-half-wave rectified and unfiltered, deeply modulated, at 37.5 or 75 Hz rate, envelope with approximately 35% average to peak power ratio; FULGURATE (or Spark-Gap Wave)-deeply modulated, 3.6 KPPS random rate with approximately 20% average to peak power ratio. Selection of the bipolar mode will automatically select the HEMO mode.

The RF power generating circuitry may be of the well known tube-type described in U.S. Pat. No. 3,730,188, whose contents are herein incorporated by reference, which is capable of generating a fully-rectified, filtered RF current for cutting, a full-wave rectified current for combining cutting and coagulation, and a half-wave rectified current for coagulation. Alternatively, the RF power generating circuitry can be of the well-known solid-state type capable of generating the same kinds of waveforms. The RF circuitry, as such, is not part of the present invention, as such circuits are well-known in the prior art. What is a feature of the invention is that the RF circuitry provides two different frequencies of operation, a first high frequency in the range of 3.8–4.0 MHz, and a second high frequency in the range of 1.7–2.0 MHz, which is easily obtained by providing a known RF generator that provides a first and second outputs at the first and second higher frequencies and providing a simple known divide-by-two circuit for obtaining a second output at one half of the first or second frequency. Both outputs can be separately amplified and processed and made available at the console's output connectors depending on the swiches activated.

After the modulated carrier has been generated at 58, it is processed through a standard driver 60, a transformer 62, and a power amplifier 64 controlled by a bias signal and whose input is monitored for safety's sake by a power tester circuit 66 under control of the CPU. The power amplifier output 68 is inputted to a mode selection block 70 under control of the CPU 71. The mode selection is made by the user by activating the upper panel 72 by pressing switch 16 in the upper panel, or the lower panel 74 by pressing switch 16 in the lower panel. That selection, made in conjunction with the selection 42, directs the output RF energy along the upper branch 76 or the lower branch 78. Both branches contain an isolation transformer 80 and a sensor 82 for operating indicators and preventing both branches from being activated at the same time. In other words, when the monopolar sensor 82 senses RF energy, the bipolar branch is disabled, and when the bipolar sensor 82 senses RF energy, the monopolar branch is disabled. The outputs 84, 86 shown at the right are directed to the connectors 20 and 22, respectively.

Figure 3:
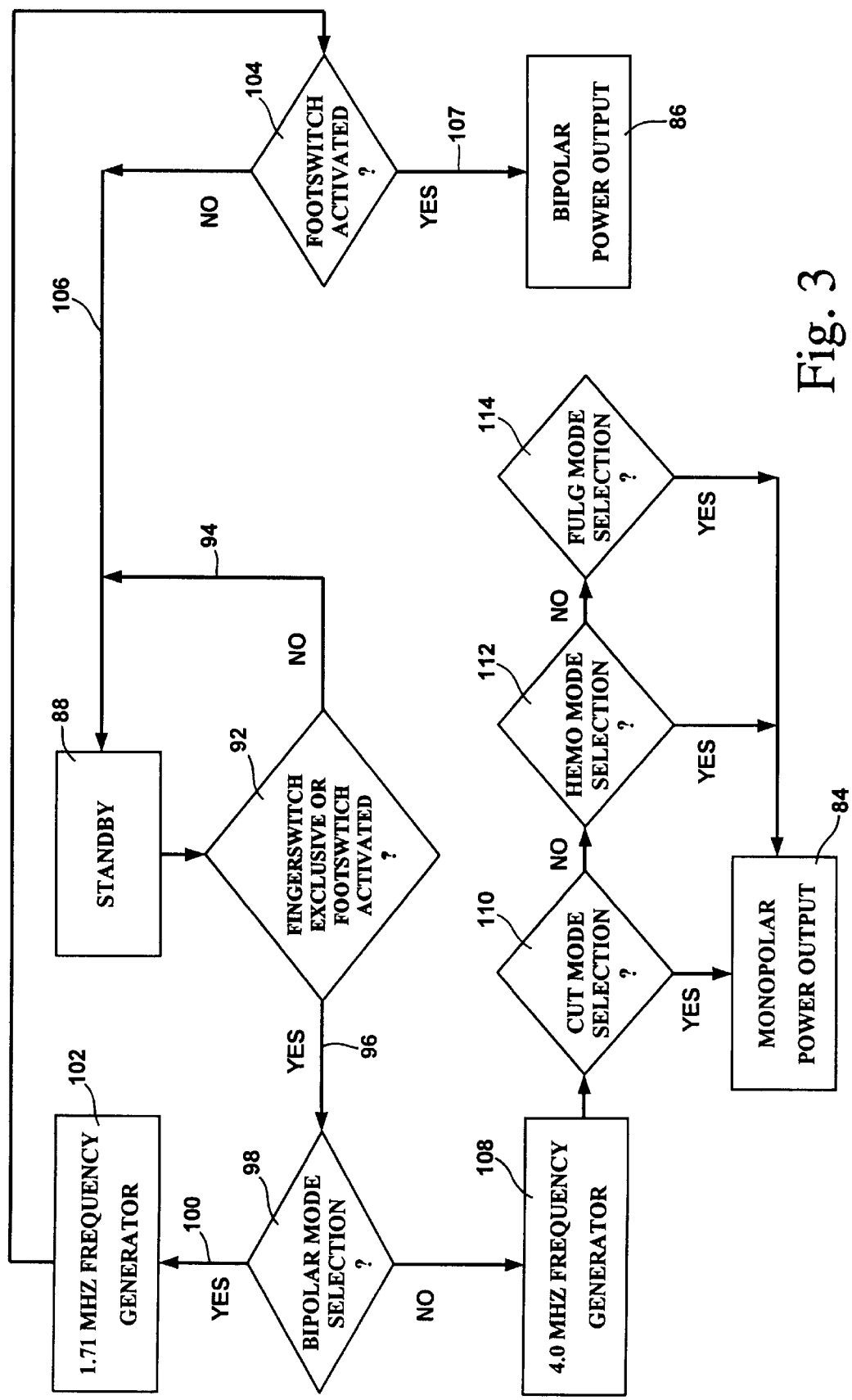
FIG. 3 is a flow chart illustrating how the system circuitry of FIG. 2 can be software controlled and operated in accordance with the invention.

In the preferred embodiment, the instrument is software controlled with the user supplying the switch inputs. One form of software control is illustrated by the flow chart depicted in FIG. 3. When the on-off switch 32 is toggled on, the microcontroller (not shown) is placed in its standby condition represented by block 88.The first action by the user is to select cutting mode or coagulation mode by pressing the footswitch 90 on the front panel, then pressing the upper or lower select switch 16 which determines which of the cutting or coagulation modes will be operable. If the coagulation mode is selected, the lower select switch 16 is used to to select unipolar (HEMO or FULGURATE) or bipolar mode. The fingerswitch handpiece 26 operates exclusively of and independent from the footswitch mode selection 90 for all unipolar modes. This ensures that RF currents are available exclusively and at all times at one of the sockets 20, 22. If no such user action has occurred, tested at block 92, the CPU returns 94 to its standby condition. If a selection has been made 96, control is passed to the test block 98, which tests whether lower switch 16 has selected the bipolar mode. If yes 100, the circuitry to generate the 1.7 MHz carrier is selected at block 102, and control passes to the test block 104 which tests whether the footswitch 34 has been pressed, which is the only way by which 1.7 MHz currents can be made available at the bipolar handpiece socket 22. If no, the CPU returns 106 to its standby mode; if yes 107, RF energy is supplied to the bipolar handpiece socket 22.

If the bipolar mode was not selected at test block 98, then the circuitry to generate the 4.0 MHz carrier is selected at block 108, and control passes to a series of test blocks 110, 112, 114 which test, respectively, whether the CUT, HEMO, or FULGURATE modes have been selected by the user by means of upper and lower switches 16, which then provide the RF energy at 4.0 Mhz at the monopolar connector output 20. If also the footswitch 34 was pressed, then the footswitch 34 can control when the RF energy is supplied to the handpiece 26; otherwise, the fingerswitch 26 on the unipolar handpiece 26 contols the delivery of RF energy to the patient.

In operation, the ground plate 30 is always attached to the patient, and the surgeon can perform any desired unipolar or bipolar electrosurgical procedure. When both the unipolar and bipolar handpieces are plugged into the instrument console 12, then the desired operating conditions for each can be preset as desired. Then whichever handpiece is picked up and operated by the surgeon will automatically determine which is supplied with the appropriate RF currents. Thus, if the bipolar handpiece is selected and the footswitch activated, the bipolar handpiece will be supplied with 1.7 Mhz currents at the power setting selected by the user. On the other hand, if the unipolar handpiece is selected and its fingerswitch 36 activated, the unipolar handpiece will be supplied with 4.0 Mhz currents at the power setting selected by the user. This operates on a first-come, first-served basis, which thus allows the surgeon to use the CUT mode for cutting with the unipolar handpiece followed with the bipolar handpiece for closing off any bleeders exposed during the cutting.

While the invention has been described in connection with the circuit of FIG. 2, wherein separate modulator and driver circuits are provided to furnish the desired output modulated waveform in accordance with the mode selected by the user, it is also possible, similar to what is described in the referenced U.S. Pat. No. 3,730,188, to provide the desired modulation by directly modulating the power supply for the power amplifier.

The construction of the invention offers the advantages of ready accessibility and versatility: accessibility, as the user is able to exercise either handpiece without touching anything else, simplifying greatly maintaining sterile fields; versatility, as the adjustability from one electrosurgical mode to another mode is extremely simple.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. An electrosurgical instrument for selectively providing RF power to operate a unipolar handpiece and a bipolar forceps, comprising:
   (a) a console,
   (b) RF power generating circuitry inside the console and capable of generating electrosurgical currents at a first frequency and at a different second frequency,
   (c) first electrical connectors at the console for receiving a unipolar handpiece,
   (d) second electrical connectors at the console for receiving a bipolar forceps,
   e) first means for controlling the output power of the electrosurgical currents at the first frequency and for supplying the controlled electrosurgical currents at the first frequency to the first electrical connectors,
   f) second means for controlling the output power of the electrosurgical currents at the second frequency and for supplying the controlled electrosurgical currents at the second frequency to the second electrical connectors,
   whereby the unipolar handpiece can be operated at a frequency different from that of the bipolar forceps.

2. An electrosurgical instrument according to claim 1, further comprising a footswitch and third electrical connectors at a side of the console for connection to the footswitch, said footswitch functioning to turn on and off the RF power generating circuitry.

3. An electrosurgical instrument according to claim 2, further comprising a unipolar handpiece, wherein said unipolar handpiece comprises a fingerswitch, said fingerswitch functioning to turn on and off the RF power generating circuitry.

4. An electrosurgical instrument according to claim 3, further comprising means for preventing both the footswitch and fingerswitch to cause simultaneous supply of electrosurgical currents at both the first and second connectors.

5. An electrosurgical instrument according to claim 3, further comprising means for causing the bipolar handpiece to be activated only by the footswitch.

6. An electrosurgical instrument according to claim 3, further comprising means for causing the unipolar handpiece to be activated by either the footswitch or the fingerswitch.

7. An electrosurgical instrument according to claim 1, wherein the first frequency is higher than that of the second frequency.

8. An electrosurgical instrument according to claim 7, wherein the first frequency is in the range of about 3.8–4.0 Mhz, and the second frequency is in the range of about 1.7–2.0 MHz.

9. A method for treating patients with electrosurgical currents from an electrosurgical instrument for selectively providing RF power to operate a unipolar handpiece and a bipolar forceps, comprising the steps:
   (a) operating the electrosurgical instrument to generate electrosurgical currents at a first frequency in a procedure for cutting tissue of the patient using a unipolar handpiece wherein bleeders may be formed,
   (b) operating the electrosurgical instrument to generate electrosurgical currents at a second different frequency in a procedure for coagulating the bleeders using a bipolar handpiece.

10. The method of claim 9, wherein the first frequency is in the range of about 3.84–4.0 Mhz, and the second frequency is in the range of about 1.7–2.0 MHz.

11. An electrosurgical instrument for selectively providing RF power to operate a unipolar handpiece and a bipolar handpiece, comprising:
   (a) a console,
   (b) RF power generating circuitry inside the console and capable of generating RF electrosurgical currents at a first frequency at a first console output and RF electrosurgical currents at a different second frequency at a second console output,
   (c) a unipolar handpiece adapted for connection to the first output,
   (d) a bipolar handpiece adapted for connection to the second output,
   e) means for selectively supplying electrosurgical currents at the first frequency to the first output and electrosurgical currents at the second frequency to the second output, respectively,
   whereby when the unipolar handpiece is connected to the first output it can be supplied with RF electrosurgical currents at the first frequency and when the bipolar handpiece is connected to the second output it can be supplied with RF electrosurgical currents at a frequency different from that supplied to the unipolar handpiece.

12. A method for treating patients with electrosurgical currents from an electrosurgical instrument for selectively providing RF power to operate a unipolar handpiece and a bipolar handpiece, comprising the steps:

(a) supplying at a first output of the electrosurgical instrument RF electrosurgical currents at a first frequency, (b) supplying at a second output of the electrosurgical instrument RF electrosurgical currents at a second different frequency, (c) connecting the unipolar handpiece to the first output to treat the patient with RF electrosurgical currents at the first frequency via the unipolar handpiece, (d) connecting the bipolar handpiece to the second output to treat the patient with RF electrosurgical currents at the second different frequency via the bipolar handpiece.

\* \* \* \* \*